(12) United States Patent
Zhang

(10) Patent No.: US 11,236,292 B1
(45) Date of Patent: Feb. 1, 2022

(54) PERFUMED LATEX SOAP AND PREPARATION METHOD THEREOF

(71) Applicant: Wenzhou Jiabo Latex Products Co., Ltd., Wanquan Township, Pingyang County (CN)

(72) Inventor: Liwen Zhang, Ruian (CN)

(73) Assignee: Wenzhou Jiabo Latex Products Co., Ltd., Wanquan Town (CN)

( * ) Notice: Subject to any disclaimer, the term of this patent is extended or adjusted under 35 U.S.C. 154(b) by 0 days.

(21) Appl. No.: 17/137,474

(22) Filed: Dec. 30, 2020

(30) Foreign Application Priority Data

Oct. 27, 2020 (CN) .......................... 202011155362.X

(51) Int. Cl.

| | |
|---|---|
| *A61K 8/00* | (2006.01) |
| *C11D 9/44* | (2006.01) |
| *C11D 9/38* | (2006.01) |
| *C11D 9/00* | (2006.01) |
| *C11D 9/26* | (2006.01) |
| *C11D 9/32* | (2006.01) |
| *C11D 17/00* | (2006.01) |
| *C11D 9/30* | (2006.01) |
| *C11D 13/16* | (2006.01) |
| *C11D 13/22* | (2006.01) |
| *C11D 13/10* | (2006.01) |
| *C11D 9/18* | (2006.01) |
| *A61K 8/81* | (2006.01) |
| *A61K 8/02* | (2006.01) |

(52) U.S. Cl.
CPC ............ *C11D 9/442* (2013.01); *A61K 8/0204* (2013.01); *A61K 8/0266* (2013.01); *A61K 8/81* (2013.01); *C11D 9/005* (2013.01); *C11D 9/18* (2013.01); *C11D 9/265* (2013.01); *C11D 9/30* (2013.01); *C11D 9/32* (2013.01); *C11D 9/38* (2013.01); *C11D 13/10* (2013.01); *C11D 13/16* (2013.01); *C11D 13/22* (2013.01); *C11D 17/0047* (2013.01)

(58) Field of Classification Search
CPC .............. C11D 9/005; C11D 9/18; C11D 9/30
See application file for complete search history.

(56) References Cited

U.S. PATENT DOCUMENTS

2019/0254938 A1* 8/2019 Hayakawa ............... A61Q 1/02

* cited by examiner

*Primary Examiner* — Necholus Ogden, Jr.
(74) *Attorney, Agent, or Firm* — Cooper Legal Group, LLC

(57) ABSTRACT

Perfumed latex soap is prepared from the following components in parts by weight: 2-5 parts of natural latex, 5-12 parts of glycerin, 8-10 parts of sodium dodecyl sulfate, 5-10 parts of coconut oil, 6-8 parts of palm oil, 1-3 parts of titanium dioxide, 0.8-1.2 parts of ethylenediamine tetraacetic acid, 0.6-0.8 part of sulfur, and 0.8-1.0 part of radix asparagine essential oil. The perfumed latex soap is mild, safe, and non-irritating and has aroma of the natural latex. In addition, the added radix asparagine essential oil can effectively improve the skin condition of a human body without causing the human body to generate dependence. The temperature of the mixing tank in which the perfumed latex soup is prepared is convenient to adjust and materials in a mixing cylinder can be agitated and sheared during agitating, so that the materials are fully mixed and the quality of a product is improved.

7 Claims, 3 Drawing Sheets

PERFUMED LATEX SOAP AND PREPARATION METHOD THEREOF

CROSS-REFERENCE TO RELATED APPLICATIONS

The instant application claims priority to Chinese Patent Application 202011155362.X, filed on Oct. 27, 2020, which is incorporated herein by reference.

TECHNICAL FIELD

The disclosure relates to the technical field of soap, and in particular to perfumed latex soap and a preparation method thereof.

TECHNICAL BACKGROUND

Soap is a widely used cleaning product and is a necessity of livelihood. With the improvement of living standards of people, the demand of people on the functionality of the soap is also gradually increased, and soap which can only clean skin has been eliminated, while functional soap with new functions of beautifying, sterilizing and deodorizing has been pursued and loved by people. The existing functional soap on the market is liable to cause the human body to generate dependence, and the skin will deteriorate once the people stop using the soap.

Radix asparagine is the dry root tuber of Asparagus (*Asparagus officinalis* L.). The radix asparagine contains various amino acids, such as asparagine, citrulline and serine, and oligosaccharides, has the efficacy of nourishing yin, moistening dryness, clearing away lung heat and promoting body fluid production and is often used for xeropulmonary cough, diabetes due to internal thermal, fluid injury due to heat disease and dry throat and thirst.

The information disclosed in this Technical Background section is only for enhancing the understanding of the general background of the disclosure and shall not be taken as an acknowledgement or any form of suggestion that this information forms the prior art already known to a person skilled in the art.

SUMMARY

An objective of the present disclosure is to provide perfumed latex soap and a preparation method thereof to solve the problem that existing functional soap on the market is liable to cause a human body to generate dependence, and the skin will deteriorate once people stops using the soap.

In order to achieve the objective, the present disclosure provides the following technical solution:

perfumed latex soap is prepared from the following components in parts by weight: 2-5 parts of natural latex, 5-12 parts of glycerin, 8-10 parts of sodium dodecyl sulfate, 5-10 parts of coconut oil, 6-8 parts of palm oil, 1-3 parts of titanium dioxide, 0.8-1.2 parts of ethylenediamine tetraacetic acid, 0.6-0.8 part of sulfur, and 0.8-1.0 part of radix asparagine essential oil.

As a preference, the perfumed latex soap is prepared from the following components in parts by weight: 3 parts of the natural latex, 8 parts of the glycerin, 9 parts of the sodium dodecyl sulfate, 7.5 parts of the coconut oil, 7 parts of the palm oil, 2 parts of the titanium dioxide, 1 part of the ethylenediamine tetraacetic acid, 0.7 part of the sulfur, and 1 part of the radix asparagine essential oil.

As a preference, a preparation method of radix asparagine essential oil includes the following steps of: pulverizing radix asparagine to yield pulverized radix asparagine, sieving the pulverized radix asparagine with a 60-80-mesh sieve, adding water 6-8 times, performing extraction with distillation for 1.0-1.2 h, and collecting volatile oil.

The present disclosure further provides a preparation method of the perfumed latex soap, which includes the following steps of:
(1) weighing the components in parts by weight;
(2) performing deamination treatment on the natural latex to yield treated natural latex, and pouring the treated natural latex in a mixing agitator; and
(3) adding other residual components in the mixing agitator, maintaining a temperature at 55-60° C., performing agitation for 40-60 minutes at a rotating speed of 800-1200 revolutions per minute (r/min) to yield a mixed solution, introducing the mixed solution into a mold, cooling the mixed solution to a room temperature (i.e., 18° C. to 22° C.) to yield a cooled mixed solution, and cutting the cooled mixed solution into blocks to obtain the perfumed latex soap.

The disclosure further provides a concrete structure of the mixing agitator which includes:
a mixing cylinder including an outer cylinder and an inner cylinder, wherein a gap is disposed between the outer cylinder and the inner cylinder for arranging a heating wire, a bottom of the mixing cylinder communicates with a liquid guiding pipe, and a switching valve is arranged on the liquid guiding pipe;
a cylinder cover fixed at an upper end of the mixing cylinder by bolts and is provided with a feed inlet; and
agitating pieces including a driving motor, an agitating shaft, agitating blades, and agitating rods, wherein the driving motor is fixed at a middle part of the cylinder cover, an output shaft of the driving motor is arranged vertically downwards, the agitating shaft is located in the mixing cylinder and is connected to the output shaft of the driving motor through a coupling, the agitating blades are uniformly arranged in an axial direction of the agitating shaft, the agitating rods are in a shape of a figure "7", upper ends of the agitating rods are fixed at upper ends of the agitating shaft respectively, lower ends of the agitating rods extend to the bottom of the mixing cylinder, and the agitating rods are uniformly arranged in a circumferential direction of the agitating shaft.

As a preference, a gap is disposed between each agitating rod of the agitating rods and a corresponding agitating blade of the agitating blades.

As a preference, a temperature display and switches connected with the driving motor and the heating wire are arranged on a wall of the outer cylinder.

Compared with the prior art, the perfumed latex soap has the following beneficial effects:
(1) The perfumed latex soap of the present disclosure is mild, safe, and non-irritating and has aroma of the natural latex. In addition, the added radix asparagine essential oil can effectively improve the skin condition of a human body without causing the human body to generate dependence.
(2) The temperature of the mixing agitator is convenient to adjust, and materials in the mixing cylinder can be agitated and sheared during agitating, so that the materials in the cylinder are fully mixed, and improvement on the quality of a product is facilitated.

Figure 1:
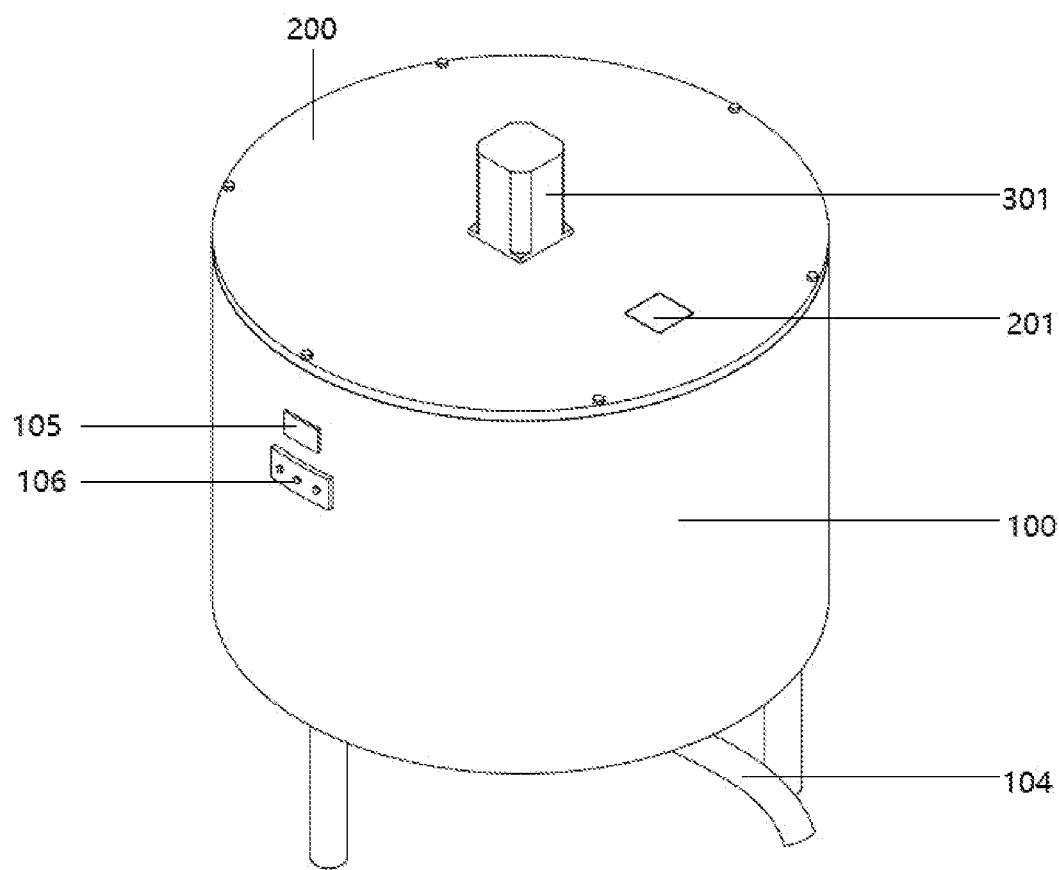
FIG. 1 is a schematic structural diagram of a mixing cylinder of the present disclosure.

100—mixing cylinder; 101—outer cylinder; 102—inner cylinder; 103—heating wire; 104—liquid guiding pipe; 105—temperature display; 106—switch; 200—cylinder cover; 201—feed inlet; 300—agitating piece; 301—driving motor; 302—agitating shaft; 303—agitating blade; 304—agitating rod.

DETAILED DESCRIPTION

The following is a clear and complete description of the technical solution of the patent of the present disclosure. The described examples are some of the examples of the present disclosure, not all of the examples of the present disclosure. Based on the examples of the present disclosure, all other examples obtained by a person skilled in the art without creative work shall fall within the protection scope of the present disclosure.

Example 1

Perfumed latex soap is prepared from the following components by weight: 2 kg of natural latex, 5 kg of glycerin, 8 kg of sodium dodecyl sulfate, 5 kg of coconut oil, 6 kg of palm oil, 1 kg of titanium dioxide, 0.8 kg of ethylenediamine tetraacetic acid, 0.6 kg of sulfur, and 0.8 kg of radix asparagine essential oil. A preparation method of the radix asparagine essential oil includes the following steps of: pulverizing radix asparagine, sieving the pulverized radix asparagine with a 60-mesh sieve, adding 6 times of water, performing extraction with distillation for 1.0 h, and collecting volatile oil.

A preparation method of the perfumed latex soap includes the following steps of:
(1) weighing various components by weight;
(2) performing deamination treatment on the natural latex, and then pouring the treated natural latex into a mixing agitator; and
(3) adding other residual components in the mixing agitator, maintaining a temperature at 55° C., performing agitation at a rotating speed of 800 r/min for 40 min, introducing a mixed solution into a mold, cooling the mixed solution to a room temperature, and cutting the cooled mixed solution into blocks to obtain the soap.

Example 2

Perfumed latex soap is prepared from the following components by weight: 3 kg of natural latex, 8 kg of glycerin, 9 kg of sodium dodecyl sulfate, 7.5 kg of coconut oil, 7 kg of palm oil, 2 kg of titanium dioxide, 1 kg of ethylenediamine tetraacetic acid, 0.7 kg of sulfur, and 1 kg of radix asparagine essential oil. A preparation method of the radix asparagine essential oil includes the following steps of: pulverizing radix asparagine, sieving the pulverized radix asparagine with a 70-mesh sieve, adding 6-8 times of water, performing extraction with distillation for 1.1 h, and collecting volatile oil.

A preparation method of the perfumed latex soap includes the following steps of: (1) weighing various components by weight;
(2) performing deamination treatment on the natural latex, and pouring the treated natural latex into a mixing agitator; and
(3) adding other residual components into the mixing agitator, maintaining a temperature at 58° C., performing agitation at a rotating speed of 1000 r/min for 50 min, introducing a mixed solution into a mold, cooling the mixed solution to a room temperature, and cutting the cooled mixed solution into blocks to obtain the soap.

Example 3

Perfumed latex soap is prepared from the following components by weight: 5 kg of natural latex, 12 kg of glycerin, 10 kg of sodium dodecyl sulfate, 10 kg of coconut oil, 8 kg of palm oil, 3 kg of titanium dioxide, 1.2 kg of ethylenediamine tetraacetic acid, 0.8 kg of sulfur, and 1.0 kg of radix asparagine essential oil. A preparation method of the radix asparagine essential oil includes the following steps of: pulverizing radix asparagine, sieving the pulverized radix asparagine with a 80-mesh sieve, adding 8 times of water, performing extraction with distillation for 1.2 h, and collecting volatile oil;

A preparation method of the perfumed latex soap includes the following steps of:
(1) weighing various components by weight;
(2) performing deamination treatment on the natural latex, and pouring the treated natural latex into a mixing agitator; and
(3) adding other residual components into the mixing agitator, maintaining a temperature at 60° C., performing agitation at a rotating speed of 1200 r/min for 60 min, introducing a mixed solution into a mold, cooling the mixed solution to a room temperature, and cutting the cooled mixed solution into blocks to obtain the soap.

Example 4

Figure 2:
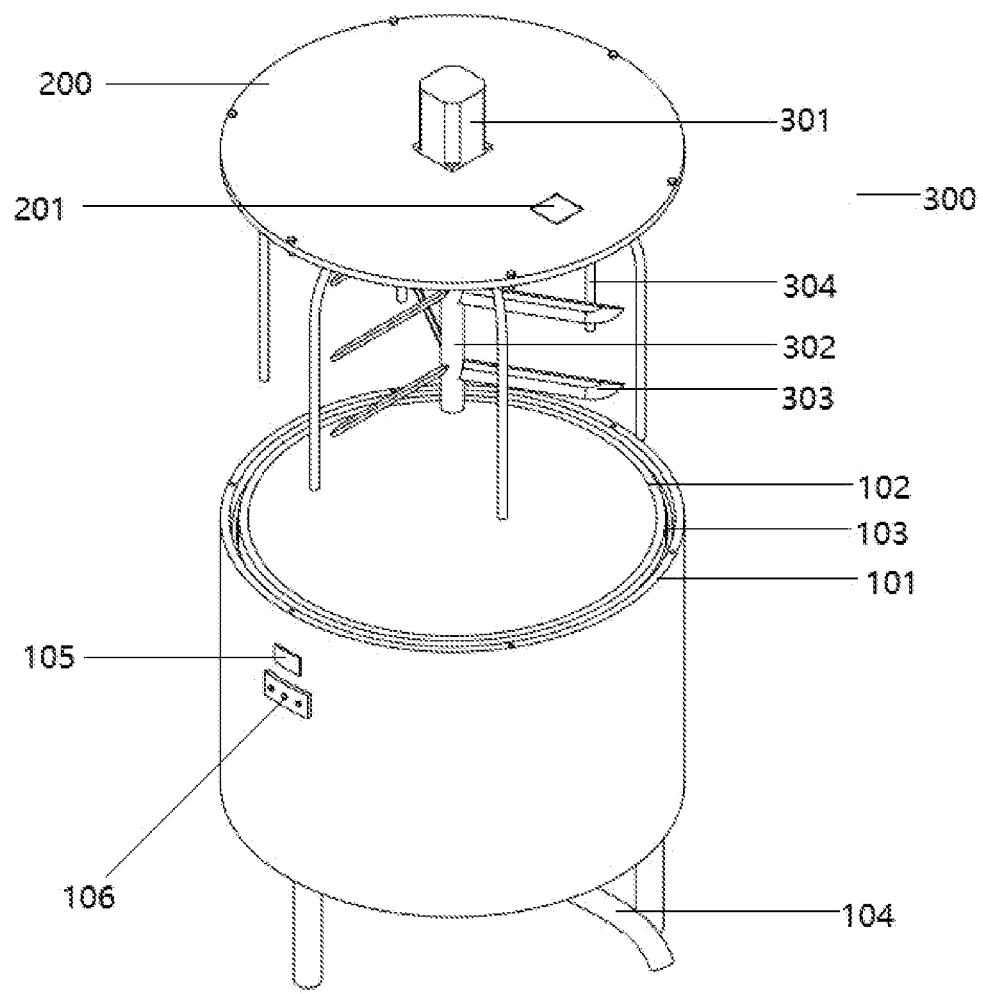
FIG. 2 is an exploded view of FIG. 1.
Figure 3:
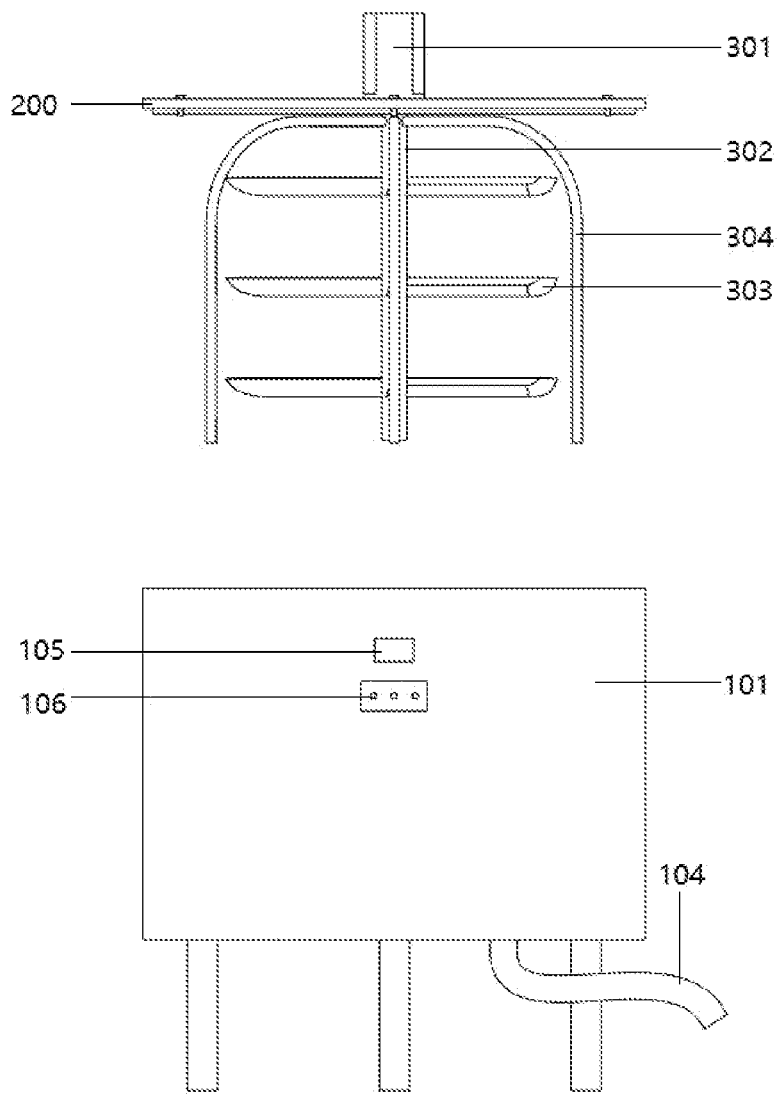
FIG. 3 is a front view of FIG. 2.

Referring to FIGS. 1-3, the mixing agitator in the above-mentioned examples includes:
a mixing cylinder 100, including an outer cylinder 101 and an inner cylinder 102, and a gap is left between the outer cylinder 101 and the inner cylinder 102 for arranging a heating wire 103; and the bottom of the mixing cylinder 100 communicates with a liquid guiding pipe 104, and switching valve (not shown in the drawing) is arranged on the liquid guiding pipe 104;
a cylinder cover 200, fixed on the upper end of the mixing cylinder 100 by bolts and provided with a feed inlet 201;
agitating piece 300, including a driving motor 301, an agitating shaft 302, agitating blades 303 and agitating rods 304, wherein the driving motor 301 is fixed at the middle part of the cylinder cover 200, and an output shaft of the driving motor 301 is arranged vertically downwards; the agitating shaft 302 is located in the mixing cylinder 100 and is connected to the output shaft of the driving motor 301 through a coupling; the agitating blades 303 are uniformly arranged in an axial direction of the agitating shaft 302; the agitating rods 304 are in a shape of a figure "7", the upper ends of the agitating rods 304 are fixed to the upper ends of the agitating shaft 302 respectively, and the lower ends of the agitating rods 304 extend to the bottom of the mixing cylinder 100; and the agitating rods 304 are uniformly arranged in a circumferential direction of the agitating shaft 302.

In this example, a gap is left between each agitating rod 304 and the corresponding agitating blade 303; and the wall of the outer cylinder 101 is provided with a temperature display 105 and switches 106 connected with the driving motor 301 and the heating wire 103. Herein, it is not difficult to understand that there are a plurality of switches 106 for controlling operation and shutdown of the driving motor 301 and the heating wire 103 respectively.

In use, the deaminated natural latex and other components are added in the inner cylinder 102 of the mixing cylinder 100, and the switches 106 for controlling the heating wire 103 and the driving motor 301 are separately turned on. When the heating wire 103 works, the materials in the inner cylinder 102 are heated, the driving motor 301 drives the agitating blades 303 and the agitating rods 304 to rotate, the agitating blades 303 and the agitating rods 304 agitate the materials in the inner cylinder 102, and at the same time, the agitating blades 303 shear the materials to enable the materials to disperse more thoroughly, so that the various materials are mixed more thoroughly, and the quality of the soap is improved. In the heating process, the temperature in the inner cylinder 102 can be obtained in real time through the temperature display 105, and the heating wire 103 can be turned off or turned on in time to adjust the temperature. After agitation is performed for a period of time, the switches 106 of the heating wire 103 and the driving motor 301 are turned off, and the materials of the inner cylinder 102 can be guided out through the liquid guiding pipe 104.

Comparative Example 1

A difference between Comparative Example 1 and Example 2 is the lack of the radix asparagine essential oil only.

Bacteriostasis Test

I. Soap for test: the soap prepared in Example 2 and the soap in Comparative Example 1.

II. Bacterial suspension for test: *Staphylococcus aureus*, *Escherichia coli* and *Candida albicans*.

III. Test Methods:

1. 10 g of the soap for test is oscillated with 50 ml distilled water in a water bath at 45° C. until the soap for test is thoroughly dissolved to obtain a soap solution for test;

2. sterile dry filter paper is put in a sterile plate, 20 μL of the soap solution for test is dripped on each sheet of filter paper, and the filter paper is dried to obtain soap filter paper sheet to be tested; and 3. a K-B paper diffusion method: the bacterial suspension with a concentration being 8×106 cfu/mL is dipped by a sterile swab, the whole surface of a nutrient agar medium plate is coated with the bacterial suspension repeatedly for 3 times, and the plate is covered and placed at a place with the room temperature for drying for 5 min; and the soap filter paper to be tested obtained in the step 2 is pasted on the plate, and a diameter of a bacteriostatic ring is measured after culturing for 24 h at 37° C. Test results are shown in Table 1 below.

TABLE 1

| | Diameter of Bacteriostatic Ring of Soap | |
|---|---|---|
| Bacterium for Test | Example 2 Diameter of Bacteriostatic Ring of Soap (mm) | Comparative Example 1 Diameter of Bacteriostatic Ring of Soap (mm) |
| *Staphylococcus aureus* | 16.38 | 9.21 |
| *Escherichia coli* | 14.47 | 4.95 |
| *Candida albicans* | 18.26 | 6.06 |

It can be seen from Table 1 that the diameter of the bacteriostatic ring of the soap of Example 2 is obviously larger than that of the soap of Comparative Example 1, which shows that the bacteriostatic effect of Example 2 is better. It also shows from another aspect that addition of the radix asparagine essential oil in the soap can improve the bacteriostatic effect of the soap.

To sum up, the perfumed latex soap of the present disclosure is mild, safe, and non-irritating and has the aroma of the natural latex. In addition, the added radix asparagine essential oil can effectively improve the skin condition of the human body without causing the human body to generate dependence.

The foregoing description of specific exemplary embodiments of the present disclosure is for illustration and exemplification. These descriptions are not intended to limit the present disclosure to the precise forms disclosed, and it is obvious that many modifications and variations can be made in light of the above teachings. The exemplary embodiments chosen and described are to explain the specific principles of the present disclosure and their practical application, so as to enable those skilled in the art to implement and utilize various exemplary embodiments as well as various choices and variations thereof. The scope of the present disclosure is intended to be defined by the claims and their equivalents.

What is claimed is:

1. Perfumed latex soap prepared from the following components in parts by weight:
  2-5 parts of natural latex,
  5-12 parts of glycerin,
  8-10 parts of sodium dodecyl sulfate,
  5-10 parts of coconut oil,
  6-8 parts of palm oil,
  1-3 parts of titanium dioxide,
  0.8-1.2 parts of ethylenediamine tetraacetic acid,
  0.6-0.8 parts of sulfur, and
  0.8-1.0 part of radix asparagine essential oil.

2. The perfumed latex soap according to claim 1, wherein the perfumed latex soap is prepared from the following components in parts by weight:
  3 parts of the natural latex,
  8 parts of the glycerin,
  9 parts of the sodium dodecyl sulfate,
  7.5 parts of the coconut oil,
  7 parts of the palm oil,
  2 parts of the titanium dioxide,
  1 part of the ethylenediamine tetraacetic acid,
  0.7 part of the sulfur, and
  1 part of the radix asparagine essential oil.

3. The perfumed latex soap according to claim 1, wherein a preparation method of the radix asparagine essential oil comprises:
  pulverizing radix asparagine to yield pulverized radix asparagine,
  sieving the pulverized radix asparagine with a 60-80 mesh sieve,
  adding water 6-8 times,
  performing extraction with distillation for 1.0-1.2 hours, and
  collecting volatile oil.

4. A preparation method of the perfumed latex soap according to claim 1, wherein the preparation method comprises:
  (1) weighing the components in parts by weight;
  (2) performing deamination treatment on the natural latex to yield treated natural latex, and then pouring the treated natural latex in a mixing agitator; and
  (3) adding other residual components in the mixing agitator, maintaining a temperature at 55-60° C., performing agitation for 40-60 minutes at a rotating speed of 800-1200 revolutions per minute (r/min) to yield a mixed solution, introducing the mixed solution into a mold, cooling the mixed solution to room temperature to yield a cooled mixed solution, and cutting the cooled mixed solution into blocks to obtain the perfumed latex soap.

5. The preparation method according to claim 4, wherein the mixing agitator comprises:
   a mixing cylinder comprising an outer cylinder and an inner cylinder, wherein a gap is disposed between the outer cylinder and the inner cylinder for arranging a heating wire, a bottom of the mixing cylinder communicates with a liquid guiding pipe, and a switching valve is arranged on the liquid guiding pipe;
   a cylinder cover fixed at an upper end of the mixing cylinder by bolts and being provided with a feed inlet; and
   agitating pieces comprising a driving motor, an agitating shaft, agitating blades, and agitating rods, wherein the driving motor is fixed at a middle part of the cylinder cover, an output shaft of the driving motor is arranged vertically downwards, the agitating shaft is located in the mixing cylinder and is connected to the output shaft of the driving motor through a coupling, the agitating blades are uniformly arranged in an axial direction of the agitating shaft, the agitating rods are in shape of a figure "7", upper ends of the agitating rods are fixed at upper ends of the agitating shaft respectively, lower ends of the agitating rods extend to the bottom of the mixing cylinder, and the agitating rods are uniformly arranged in a circumferential direction of the agitating shaft.

6. The preparation method according to claim 5, wherein a gap is disposed between each agitating rod of the agitating rods and a corresponding agitating blade of the agitating blades.

7. The preparation method according to claim 5, wherein a wall of the outer cylinder is provided with a temperature display and switches connected with the driving motor and the heating wire.

* * * * *